(12) United States Patent
Haught

(10) Patent No.: US 11,686,687 B2
(45) Date of Patent: Jun. 27, 2023

(54) OIL SIGHT GLASS

(71) Applicant: ESCO Products, Inc, Houston, TX (US)

(72) Inventor: Christopher Haught, Houston, TX (US)

( * ) Notice: Subject to any disclaimer, the term of this patent is extended or adjusted under 35 U.S.C. 154(b) by 39 days.

(21) Appl. No.: 17/114,973

(22) Filed: Dec. 8, 2020

(65) Prior Publication Data

US 2021/0223186 A1     Jul. 22, 2021

Related U.S. Application Data

(63) Continuation-in-part of application No. 29/721,673, filed on Jan. 22, 2020.

(51) Int. Cl.
*G01N 21/95* (2006.01)
*G01N 33/28* (2006.01)

(52) U.S. Cl.
CPC ............. *G01N 21/95* (2013.01); *G01N 33/28* (2013.01)

(58) Field of Classification Search
None
See application file for complete search history.

(56) References Cited

U.S. PATENT DOCUMENTS

| | | | | |
|---|---|---|---|---|
| 1,092,194 A | * | 4/1914 | Wood | F16N 13/16 184/29 |
| 3,817,205 A | * | 6/1974 | Bonetti | G01F 23/02 73/330 |
| 4,888,990 A | * | 12/1989 | Bryan | G01F 23/02 285/911 |
| D790,999 S | | 7/2017 | Haworth | |
| D792,259 S | | 7/2017 | Haworth | |
| D834,976 S | | 12/2018 | Cooper | |
| 10,451,466 B2 | | 10/2019 | Cooper | |
| 10,545,045 B2 | | 1/2020 | Fitch | |
| 2004/0118146 A1 | * | 6/2004 | Haller | F04C 23/008 62/469 |
| 2008/0066543 A1 | * | 3/2008 | Sabini | G01F 23/02 73/304 C |
| 2014/0238156 A1 | * | 8/2014 | Aljohani | G01N 1/10 73/864.63 |
| 2016/0305810 A1 | * | 10/2016 | Fitch | F16K 37/0058 |
| 2021/0188672 A1 | * | 6/2021 | Shalon | C02F 1/686 |

FOREIGN PATENT DOCUMENTS

| | | | | |
|---|---|---|---|---|
| DE | 202015002570 U1 | * | 8/2016 | |
| WO | WO-2010009590 A1 | * | 1/2010 | ............ F25B 41/006 |
| WO | WO2013048941 A1 | | 4/2013 | |

* cited by examiner

*Primary Examiner* — Rufus L Phillips

(74) *Attorney, Agent, or Firm* — Shannon Warren

(57) ABSTRACT

An oil sight glass for visual inspection of water and debris in a fluid such as oil within a reservoir to which the oil sight glass is connected. The oil sight glass comprises a sight body, a first end, a second end, a first fluid opening, a second fluid opening, a chamber, and a hex head, and a sidewall. The chamber is in fluid communication between the first fluid opening in the first end, and the second fluid opening in the second end.

8 Claims, 4 Drawing Sheets

US 11,686,687 B2

OIL SIGHT GLASS

CROSS-REFERENCE TO RELATED APPLICATIONS

This application claims benefit to U.S. application Ser. Nos. 29/721,673 and 62/945,219.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

Prior art known to the Applicant includes US20180073907, WO 2013048941, and US 20160305810, D792259, D790999, and D834976.

BRIEF SUMMARY OF THE INVENTION

An oil sight glass for visual inspection of water and debris in a fluid such as oil within a reservoir to which said oil sight glass is connected. Said oil sight glass comprises a sight body, a first end, a second end, a first fluid opening, a second fluid opening, a chamber, and a hex head, and a sidewall. Said chamber is in fluid communication between said first fluid opening in said first end, and said second fluid opening in said second end.

Said oil sight glass for visual inspection of water and debris in a fluid such as oil within a reservoir to which said oil sight glass is connected. Said oil sight glass comprises said sight body, said first end, said second end, said first fluid opening, said second fluid opening, said chamber, and said hex head, and said sidewall. Said chamber comprises a chamber draining neck. Said chamber draining neck comprises a concave indention in a first end of said chamber being aligned with a central axis. Said chamber draining neck comprises an angle relative to a perpendicular plane from said central axis. Said chamber is in fluid communication between said first fluid opening in said first end, and said second fluid opening in said second end.

Said oil sight glass for visual inspection of water and debris in a fluid such as oil within a reservoir to which said oil sight glass is connected. Said oil sight glass comprises said sight body, said first end, said second end, said first fluid opening, said second fluid opening, said chamber, and said hex head, and said sidewall. Said chamber is in fluid communication between said first fluid opening in said first end, and said second fluid opening in said second end. Said first fluid opening is aligned with said central axis, and further, centered on said hex head. Said hex head is an extension out of said first end. Said hex head is configured to allow users to tighten and/or remove said oil sight glass without damaging corresponding equipment. Said hex head is configured to receive and selectively connect to tools in order to grab and twist said oil sight glass.

DETAILED DESCRIPTION OF THE INVENTION

The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
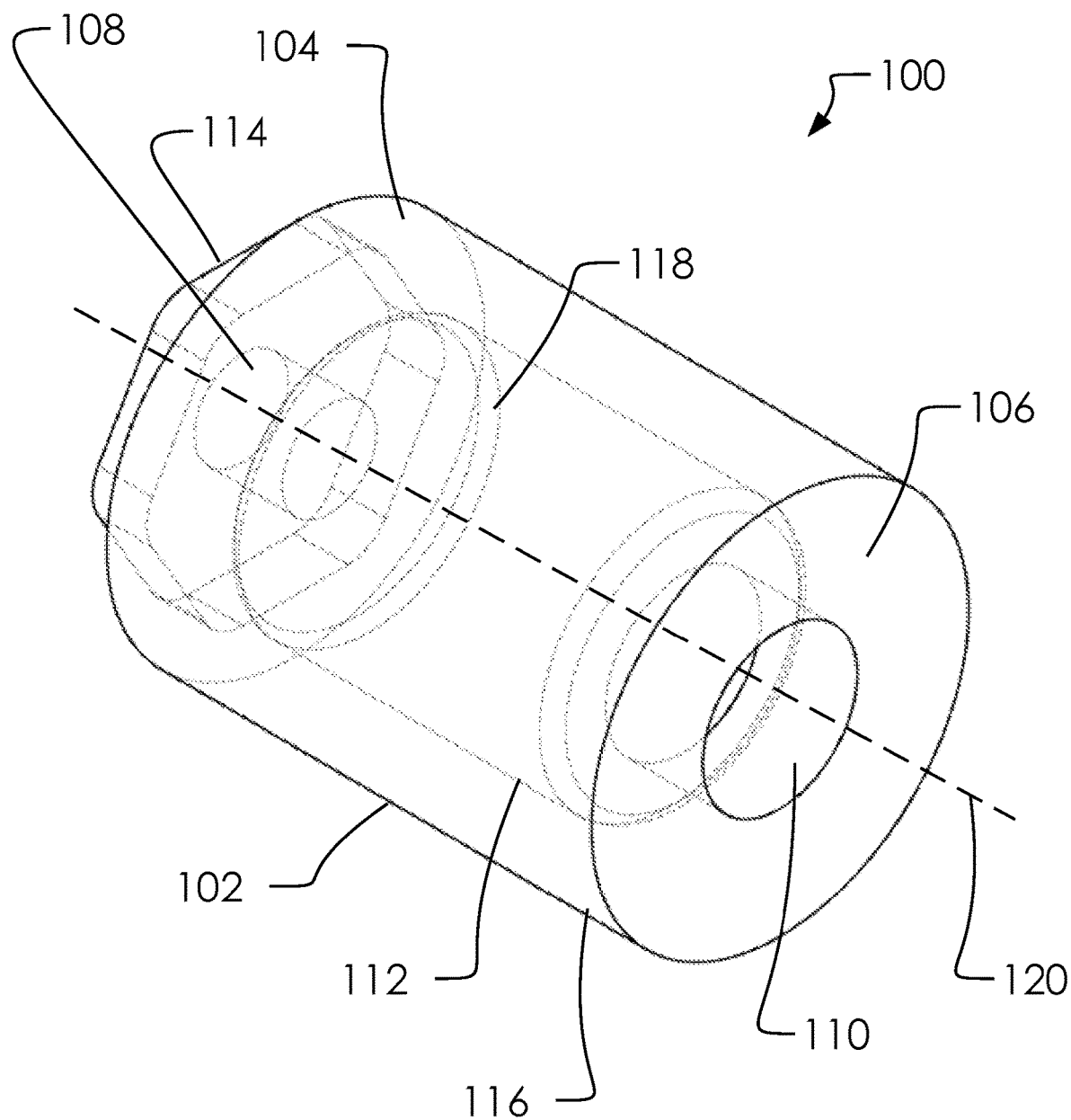
FIG. 1 illustrates a perspective overview of an oil sight glass 100.

FIG. 1 illustrates a perspective overview of an oil sight glass 100.

In one embodiment, said oil sight glass 100 can comprise a sight body 102, a first exterior end 104, a second exterior end 106, a first fluid opening 108, a second fluid opening 110, a interior fluid chamber 112, and a hex head 114, and a sidewall 116. In one embodiment, said interior fluid chamber 112 can comprise a chamber draining neck 118, as discussed herein.

In one embodiment, said oil sight glass 100 can function to provide visual confirmation of water and/or debris in a fluid such as oil. Said fluid may be stored in a reservoir (not illustrated), and said oil sight glass 100 can be connected to the reservoir with either said first exterior end 104 and said second exterior end 106. Due to wear, water, particulates, heat, etc., the fluid may become contaminated; in turn, this contaminant can migrate to the reservoir and may settle at the bottom as sediment.

This disclosure presents improvements to the prior art as to the inclusion of said chamber draining neck 118 for drainage and said hex head 114 for assistance in installation and removal of said oil sight glass 100.

In one embodiment, said sight body 102 can comprise a substantially cylindrical object between said first exterior end 104 and said second exterior end 106, aligned along a central axis 120. Said interior fluid chamber 112 can be in fluid communication between said first fluid opening 108 in said first exterior end 104104 and said second fluid opening 110 in said second exterior end 106.

Said first fluid opening 108 can be aligned with said central axis 120, and further, centered on said hex head 114. Said first fluid opening 108, said second fluid opening 110 and said interior fluid chamber 112 can all be aligned with said central axis 120.

Said hex head 114 can be an extension out of said first exterior end 104. Said oil sight glass 100 can be machined or created from an injected polymer and/or acrylic. Said sight body 102 and said hex head 114 can, consequently, be formed of the same material at the time of manufacturing.

Said hex head 114 can allow users to tighten and/or remove said oil sight glass 100 without damaging corresponding equipment. As is known in the art, oil sight glasses can become adhered to other equipment on account of temperature and chemical changes, wherein, removing a sight glass may require destroying or damaging the sight glass. By including said hex head 114, common tools can grab and twist said oil sight glass 100.

Figure 2:
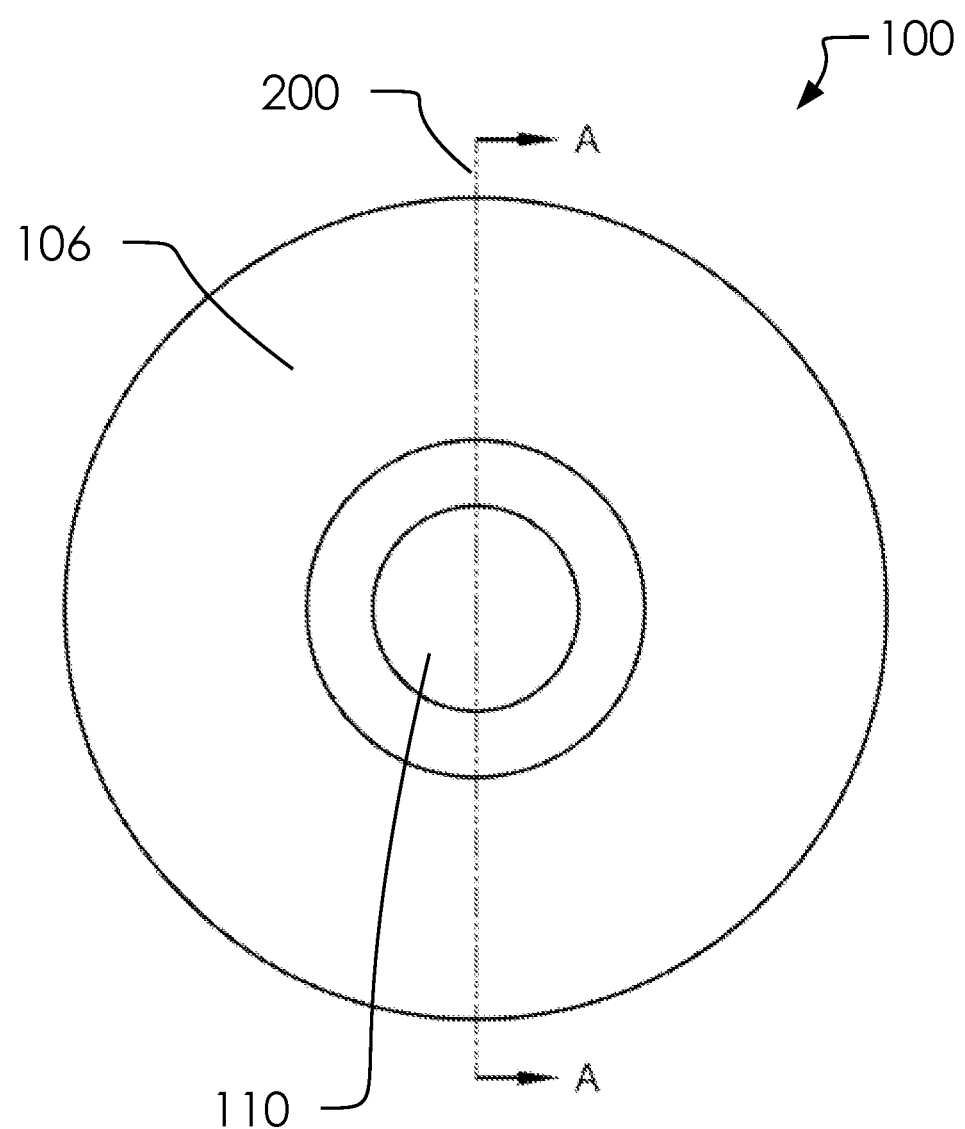
FIG. 2 illustrates an elevated first side view of said oil sight glass 100 with a section cut A line 200.

FIG. 2 illustrates an elevated first side view of said oil sight glass 100 with a section cut A line 200.

Figure 3:
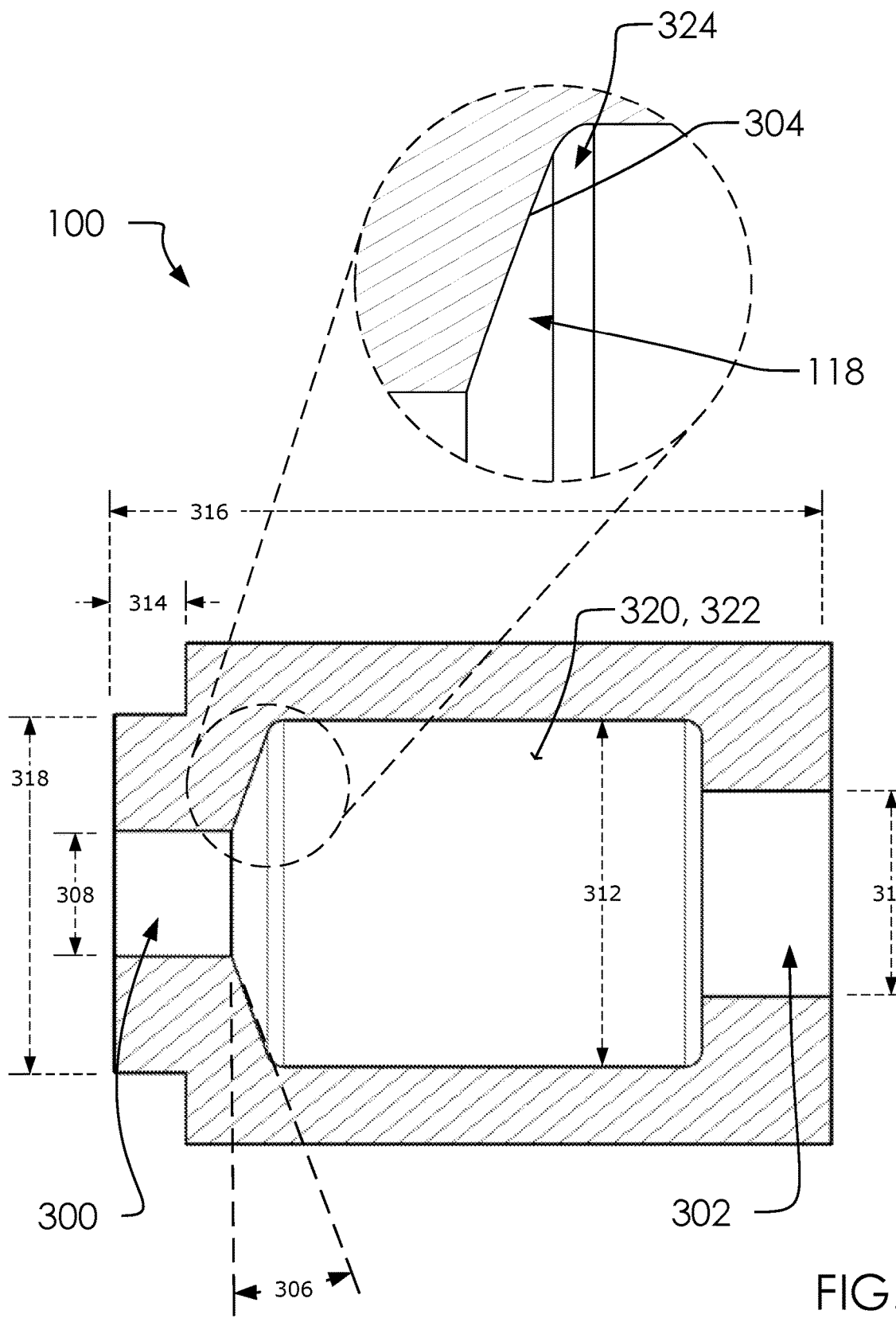
FIG. 3 illustrates an elevated cross-section front view of said oil sight glass 100.

FIG. 3 illustrates an elevated cross-section front view of said oil sight glass 100.

In one embodiment, said first fluid opening 108 can comprise a first end chamber 300 which leads into said interior fluid chamber 112, which in turn leads into a second end chamber 302 at said second fluid opening 110.

In one embodiment, said chamber draining neck 118 can comprise a concave indention in a first end 304 of said interior fluid chamber 112 being aligned with said central axis 120. In one embodiment, said chamber draining neck 118 can comprise an chamber neck angle 306 relative to a perpendicular plane from said central axis 120. In one embodiment, said chamber neck angle 306 can comprise 15-30 degrees, and in a preferred embodiment, 20 degrees. Said chamber neck angle 306 can aid in draining a fluid out of said interior fluid chamber 112 more completely that prior embodiments which were flat.

Said first end chamber 300 can comprise a first diameter 308, said second end chamber 302 can comprise a second diameter 310, said interior fluid chamber 112 can comprise a chamber diameter 312, and said hex head 114 can comprise a hex gap height 314. Said oil sight glass 100 can comprise a glass length 316, and said hex head 114 can comprise a head height 318. In one embodiment, said hex gap height 314 can comprise 1.25 inches, said chamber diameter 312 can comprise 1.2 inches, said glass length 316 can comprise 2.5 inches, and said head height 318 can comprise 0.25 inches.

Said interior fluid chamber 112 comprises a cylindrical chamber portion 320 comprising an inner wall 322 being substantially parallel with said central axis 120, said chamber draining neck 118, and said chamber draining neck 118 comprises a concave indention 324 between said cylindrical chamber portion 320 and said chamber draining neck 118 in said first chamber end of said interior fluid chamber 112 being aligned with said central axis 120.

Figure 4:
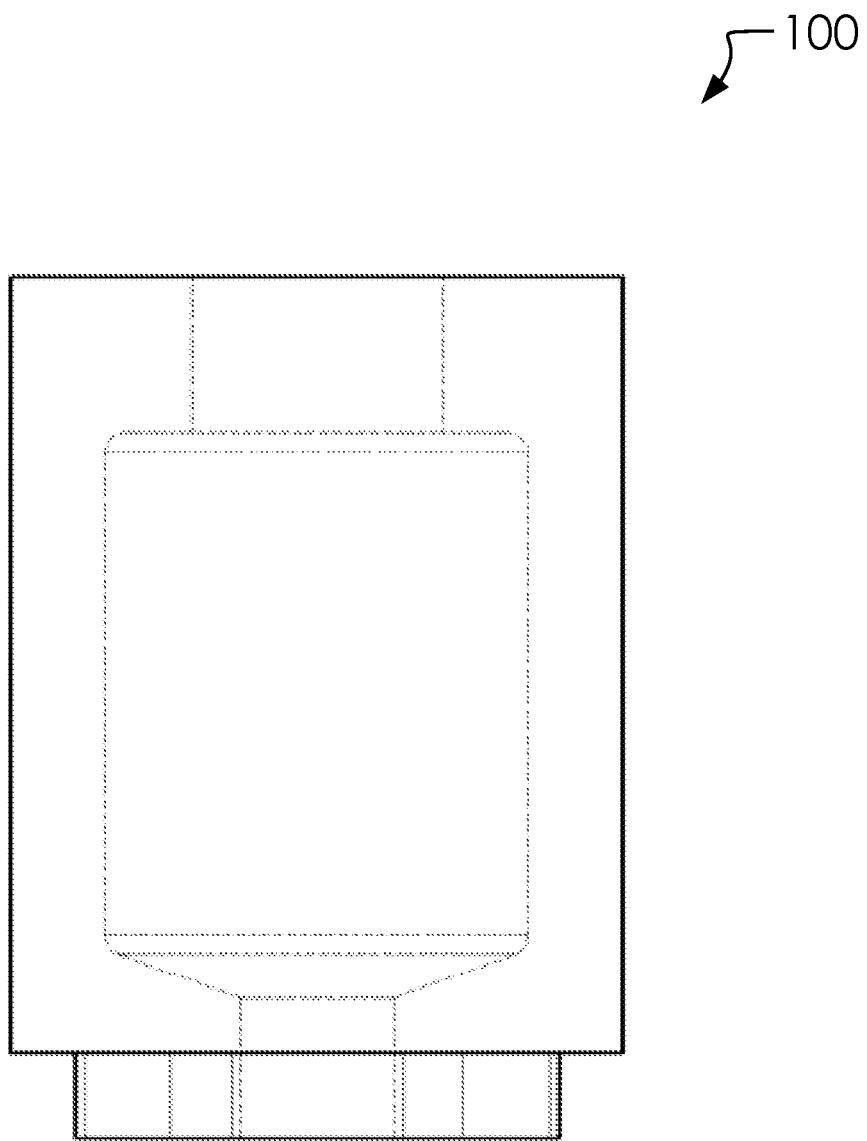
FIG. 4 illustrates an elevated top view of said oil sight glass 100.

FIG. 4 illustrates an elevated top view of said oil sight glass 100.

These parts are presented in this specification:
said oil sight glass 100,
said sight body 102,
said first exterior end 104,
said second exterior end 106,
said first fluid opening 108,
said second fluid opening 110,
said interior fluid chamber 112,
said hex head 114,
said sidewall 116,
said chamber draining neck 118,
said central axis 120,
said section cut A line 200,
said first end chamber 300,
said second end chamber 302,
said first end 304,
said chamber neck angle 306,
said first diameter 308,
said second diameter 310,
said chamber diameter 312,
said hex gap height 314,
said glass length 316,
said head height 318,
said cylindrical chamber portion 320,
said inner wall 322, and
said concave indention 324.

These sentences are presented with reference to the original claims to ensure the specification contains the contents of the claims:

Said oil sight glass 100 for visual inspection of water and debris in a fluid such as oil within a reservoir to which said oil sight glass 100 can be connected. Said oil sight glass 100 comprises said sight body 102, said first exterior end 104, said second exterior end 106, said first fluid opening 108, said second fluid opening 110, said interior fluid chamber 112, and said hex head 114, and said sidewall 116. Said interior fluid chamber 112 can be in fluid communication between said first fluid opening 108 in said first exterior end 104, and said second fluid opening 110 in said second exterior end 106.

Said interior fluid chamber 112 comprises said chamber draining neck 118.

Said oil sight glass 100 can be connected to the reservoir with either said first exterior end 104 and said second exterior end 106.

Said sight body 102 comprises a substantially cylindrical object between said first exterior end 104 and said second exterior end 106. Said sight body 102 can be aligned along said central axis 120.

Said first fluid opening 108 can be aligned with said central axis 120, and further, centered on said hex head 114. Said first fluid opening 108, said second fluid opening 110 and said interior fluid chamber 112 can be configured to all be aligned with said central axis 120.

Said hex head 114 can be an extension out of said first exterior end 104.

Said oil sight glass 100 can be machined or created from a material selected among an injected polymer and acrylic.

Said sight body 102 and said hex head 114 can be formed of the same material as said oil sight glass 100 at the time of manufacturing.

Said hex head 114 can be configured to allow users to tighten and/or remove said oil sight glass 100 without damaging corresponding equipment. Said hex head 114 can be configured to receive and selectively connect to tools in order to grab and twist said oil sight glass 100.

Said first fluid opening 108 comprises said first end chamber 300 which leads into said interior fluid chamber 112, which in turn leads into said second end chamber 302 at said second fluid opening 110.

Said chamber draining neck 118 comprises a concave indention in said first end 304 of said interior fluid chamber 112 being aligned with said central axis 120. Said chamber draining neck 118 comprises said chamber neck angle 306 relative to a perpendicular plane from said central axis 120.

Said chamber neck angle 306 comprises 15-30 degrees.

Said chamber neck angle 306 comprises 20 degrees.

Said oil sight glass 100 for visual inspection of water and debris in a fluid such as oil within a reservoir to which said oil sight glass 100 can be connected. Said oil sight glass 100 comprises said sight body 102, said first exterior end 104, said second exterior end 106, said first fluid opening 108, said second fluid opening 110, said interior fluid chamber 112, and said hex head 114, and said sidewall 116. Said interior fluid chamber 112 comprises said chamber draining neck 118. Said chamber draining neck 118 comprises a concave indention in said first end 304 of said interior fluid chamber 112 being aligned with said central axis 120. Said chamber draining neck 118 comprises said chamber neck angle 306 relative to a perpendicular plane from said central axis 120. Said interior fluid chamber 112 can be in fluid communication between said first fluid opening 108 in said first exterior end 104, and said second fluid opening 110 in said second exterior end 106.

Said oil sight glass 100 for visual inspection of water and debris in a fluid such as oil within a reservoir to which said oil sight glass 100 can be connected. Said oil sight glass 100 comprises said sight body 102, said first exterior end 104, said second exterior end 106, said first fluid opening 108, said second fluid opening 110, said interior fluid chamber 112, and said hex head 114, and said sidewall 116. Said interior fluid chamber 112 can be in fluid communication between said first fluid opening 108 in said first exterior end 104, and said second fluid opening 110 in said second exterior end 106. Said first fluid opening 108 can be aligned with said central axis 120, and further, centered on said hex head 114. Said hex head 114 can be an extension out of said first exterior end 104. Said hex head 114 can be configured to allow users to tighten and/or remove said oil sight glass 100 without damaging corresponding equipment. Said hex head 114 can be configured to receive and selectively connect to tools in order to grab and twist said oil sight glass 100.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. An oil sight glass for visual inspection of water and debris in a fluid such as oil within a reservoir to which said oil sight glass is connected; wherein,
   said oil sight glass comprises a sight body, a first exterior end, a second exterior end, a first fluid opening, a second fluid opening, an interior fluid chamber, and a hex head, and a sidewall;
   said interior fluid chamber is in fluid communication between said first fluid opening in said first exterior end, and said second fluid opening in said second exterior end;
   said sight body is aligned along a central axis;
   said first fluid opening, said second fluid opening, said hex head and said interior fluid chamber are aligned with said central axis;
   an exterior portion of said sight body at said first exterior end comprises said hex head comprising a hexagonal cross-section perpendicular to said central axis;
   said hex head is configured to receive and selectively connect to tools to grab and twist said oil sight glass; and
   said oil sight glass comprises a material selected among an injected polymer and acrylic;
   said interior fluid chamber comprises a chamber draining neck at a first end of said interior fluid chamber;
   with said oil sight glass installed with said first exterior end of said interior fluid chamber oriented at the bottom of said interior fluid chamber, said chamber draining neck is configured to drain fluids in said interior fluid chamber into said first fluid opening at said first exterior end of said oil sight glass;
   said interior fluid chamber comprises
      a cylindrical chamber portion comprising an inner wall being substantially parallel with said central axis,
      said chamber draining neck, and
      a concave indention between said cylindrical chamber portion and said chamber draining neck; and
   said draining neck comprises a chamber neck angle relative to a perpendicular plane from said central axis.

2. The oil sight glass of claim 1, wherein:
   and said oil sight glass is connected to the reservoir with either said first exterior end and said second exterior end.

3. The oil sight glass of claim 1, wherein:
   an exterior portion of said sight body comprises
      a hexagonal portion comprising said hex head, and
      a cylindrical portion comprising a substantially cylindrical shape in said sidewall at second exterior end.

4. The oil sight glass of claim 1, wherein:
   said sight body and said hex head are unibody being formed of the same material.

5. The oil sight glass of claim 1, wherein:
   said hex head is configured to allow users to tighten and remove said oil sight glass without damaging said oil sight glass since said oil sight glass rotates in its entirety by rotating said hex head.

6. The oil sight glass of claim 1, wherein:
   said first fluid opening comprises a first end chamber which leads into said interior fluid chamber, which in turn leads into a second exterior end chamber at said second fluid opening.

7. The oil sight glass of claim 1, wherein: said chamber neck angle comprises 15-30 degrees.

8. The oil sight glass of claim 1, wherein: said chamber neck angle comprises 20 degrees.

* * * * *